(12) United States Patent
Braido et al.

(10) Patent No.: US 11,147,666 B2
(45) Date of Patent: Oct. 19, 2021

(54) LEAFLET ABRASION MITIGATION IN PROSTHETIC HEART VALVES

(71) Applicant: St. Jude Medical, Cardiology Division, Inc., St. Paul, MN (US)

(72) Inventors: Peter N. Braido, Wyoming, MN (US); Kent J. Smith, Shoreview, MN (US); Andrea L. McCarthy, Vadnais Heights, MN (US); Mina S. Fahim, Shoreview, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 31 days.

(21) Appl. No.: 16/254,000

(22) Filed: Jan. 22, 2019

(65) Prior Publication Data

US 2019/0151082 A1   May 23, 2019

Related U.S. Application Data

(62) Division of application No. 14/684,589, filed on Apr. 13, 2015, now Pat. No. 10,226,332.

(60) Provisional application No. 61/979,072, filed on Apr. 14, 2014.

(51) Int. Cl.
   *A61F 2/24*   (2006.01)

(52) U.S. Cl.
   CPC .......... *A61F 2/2412* (2013.01); *A61F 2/2418* (2013.01); *A61F 2220/0075* (2013.01); *A61F 2230/0054* (2013.01); *A61F 2250/0021* (2013.01)

(58) Field of Classification Search
   CPC .................................... A61F 2/2418
   See application file for complete search history.

(56) References Cited

U.S. PATENT DOCUMENTS

| 3,657,744 A | 4/1972 | Ersek |
| 4,491,986 A | 1/1985 | Gabbay |
| 4,759,758 A | 7/1988 | Gabbay |

(Continued)

FOREIGN PATENT DOCUMENTS

| DE | 19857887 A1 | 7/2000 |
| DE | 10121210 A1 | 11/2002 |

(Continued)

OTHER PUBLICATIONS

Andersen, H.R. et al, "Transluminal implantation of artificial heart valves," European Heart Journal, May 1992, pp. 704-708, vol. 13, No. 5.

(Continued)

*Primary Examiner* — Jacqueline Woznicki
(74) *Attorney, Agent, or Firm* — Lerner, David, Littenberg, Krumholz & Mentlik, LLP (57) ABSTRACT

A prosthetic heart valve includes a stent extending in a longitudinal direction, the stent being formed of a plurality of struts forming cells and having a plurality of commissure features, a collapsed condition and an expanded condition. A valve assembly may be secured to the stent, the valve assembly including a cuff and a plurality of leaflets. The cuff may be formed of a fabric and a second material different from the fabric, the cuff having commissure peaks and a plurality of midpeaks disposed between the commissure peaks. Each of the leaflets may have a free edge.

8 Claims, 8 Drawing Sheets

(56) References Cited

U.S. PATENT DOCUMENTS

| | | | |
|---|---|---|---|
| 4,878,906 A | 11/1989 | Lindemann et al. | |
| 4,922,905 A | 5/1990 | Strecker | |
| 4,994,077 A | 2/1991 | Dobben | |
| 5,411,552 A | 5/1995 | Andersen et al. | |
| 5,480,423 A | 1/1996 | Ravenscroft et al. | |
| 5,606,928 A * | 3/1997 | Religa | A61F 2/2412 112/475.08 |
| 5,843,167 A | 12/1998 | Dwyer et al. | |
| 5,855,601 A | 1/1999 | Bessler et al. | |
| 5,935,163 A | 8/1999 | Gabbay | |
| 5,961,549 A | 10/1999 | Nguyen et al. | |
| 6,077,297 A | 6/2000 | Robinson et al. | |
| 6,083,257 A | 7/2000 | Taylor et al. | |
| 6,090,140 A | 7/2000 | Gabbay | |
| 6,214,036 B1 | 4/2001 | Letendre et al. | |
| 6,264,691 B1 | 7/2001 | Gabbay | |
| 6,267,783 B1 | 7/2001 | Letendre et al. | |
| 6,368,348 B1 | 4/2002 | Gabbay | |
| 6,419,695 B1 | 7/2002 | Gabbay | |
| 6,468,660 B2 | 10/2002 | Ogle et al. | |
| 6,488,702 B1 | 12/2002 | Besselink | |
| 6,517,576 B2 | 2/2003 | Gabbay | |
| 6,533,810 B2 | 3/2003 | Hankh et al. | |
| 6,582,464 B2 | 6/2003 | Gabbay | |
| 6,610,088 B1 | 8/2003 | Gabbay | |
| 6,623,518 B2 | 9/2003 | Thompson et al. | |
| 6,685,625 B2 | 2/2004 | Gabbay | |
| 6,719,789 B2 | 4/2004 | Cox | |
| 6,730,118 B2 | 5/2004 | Spenser et al. | |
| 6,783,556 B1 | 8/2004 | Gabbay | |
| 6,790,230 B2 | 9/2004 | Beyersdorf et al. | |
| 6,814,746 B2 | 11/2004 | Thompson et al. | |
| 6,830,584 B1 | 12/2004 | Seguin | |
| 6,869,444 B2 | 3/2005 | Gabbay | |
| 6,893,460 B2 | 5/2005 | Spenser et al. | |
| 6,908,481 B2 | 6/2005 | Cribier | |
| 7,018,406 B2 | 3/2006 | Seguin et al. | |
| 7,025,780 B2 | 4/2006 | Gabbay | |
| 7,137,184 B2 | 11/2006 | Schreck | |
| 7,160,322 B2 | 1/2007 | Gabbay | |
| 7,247,167 B2 | 7/2007 | Gabbay | |
| 7,267,686 B2 | 9/2007 | DiMatteo et al. | |
| 7,311,730 B2 | 12/2007 | Gabbay | |
| 7,329,278 B2 | 2/2008 | Seguin et al. | |
| 7,374,573 B2 | 5/2008 | Gabbay | |
| 7,381,218 B2 | 6/2008 | Schreck | |
| 7,452,371 B2 | 11/2008 | Pavcnik et al. | |
| 7,510,572 B2 | 3/2009 | Gabbay | |
| 7,524,331 B2 | 4/2009 | Birdsall | |
| RE40,816 E | 6/2009 | Taylor et al. | |
| 7,585,321 B2 | 9/2009 | Cribier | |
| 7,682,390 B2 | 3/2010 | Seguin | |
| 7,731,742 B2 | 6/2010 | Schlick et al. | |
| 7,803,185 B2 | 9/2010 | Gabbay | |
| 7,846,203 B2 | 12/2010 | Cribier | |
| 7,846,204 B2 | 12/2010 | Letac et al. | |
| 7,914,569 B2 | 3/2011 | Nguyen et al. | |
| D648,854 S | 11/2011 | Braido | |
| D652,926 S | 1/2012 | Braido | |
| D652,927 S | 1/2012 | Braido et al. | |
| D653,341 S | 1/2012 | Braido et al. | |
| D653,342 S | 1/2012 | Braido et al. | |
| D653,343 S | 1/2012 | Ness et al. | |
| D654,169 S | 2/2012 | Braido | |
| D654,170 S | 2/2012 | Braido et al. | |
| D660,432 S | 5/2012 | Braido | |
| D660,433 S | 5/2012 | Braido et al. | |
| D660,967 S | 5/2012 | Braido et al. | |
| 8,632,586 B2 | 1/2014 | Spenser et al. | |
| 9,820,852 B2 * | 11/2017 | Braido | A61F 2/2403 |
| 9,949,825 B2 * | 4/2018 | Braido | A61F 2/2418 |
| 10,238,486 B2 * | 3/2019 | Huynh | A61F 2/2409 |
| 2002/0036220 A1 | 3/2002 | Gabbay | |
| 2003/0023303 A1 | 1/2003 | Palmaz et al. | |
| 2003/0050694 A1 | 3/2003 | Yang et al. | |
| 2003/0130726 A1 | 7/2003 | Thorpe et al. | |
| 2004/0049262 A1 | 3/2004 | Obermiller et al. | |
| 2004/0093075 A1 | 5/2004 | Kuehne | |
| 2004/0186563 A1 * | 9/2004 | Lobbi | A61F 2/2427 623/2.11 |
| 2004/0210304 A1 | 10/2004 | Seguin et al. | |
| 2005/0096726 A1 | 5/2005 | Sequin et al. | |
| 2005/0137695 A1 * | 6/2005 | Salahieh | A61F 2/2418 623/2.11 |
| 2005/0137697 A1 | 6/2005 | Salahieh et al. | |
| 2005/0256566 A1 | 11/2005 | Gabbay | |
| 2006/0008497 A1 | 1/2006 | Gabbay | |
| 2006/0020327 A1 * | 1/2006 | Lashinski | A61F 2/2439 623/1.25 |
| 2006/0074484 A1 | 4/2006 | Huber | |
| 2006/0122692 A1 | 6/2006 | Gilad et al. | |
| 2006/0149360 A1 | 7/2006 | Schwammenthal et al. | |
| 2006/0173532 A1 | 8/2006 | Flagle et al. | |
| 2006/0178740 A1 | 8/2006 | Stacchino et al. | |
| 2006/0206202 A1 | 9/2006 | Bonhoeffer et al. | |
| 2006/0241744 A1 | 10/2006 | Beith | |
| 2006/0241745 A1 | 10/2006 | Solem | |
| 2006/0259120 A1 | 11/2006 | Vongphakdy et al. | |
| 2006/0259137 A1 | 11/2006 | Artof et al. | |
| 2006/0265056 A1 | 11/2006 | Nguyen et al. | |
| 2006/0276813 A1 | 12/2006 | Greenberg | |
| 2006/0293745 A1 * | 12/2006 | Carpentier | A61F 2/24 623/2.19 |
| 2007/0010876 A1 | 1/2007 | Salahieh et al. | |
| 2007/0027534 A1 | 2/2007 | Bergheim et al. | |
| 2007/0043435 A1 | 2/2007 | Seguin et al. | |
| 2007/0055358 A1 | 3/2007 | Krolik et al. | |
| 2007/0067029 A1 | 3/2007 | Gabbay | |
| 2007/0093890 A1 | 4/2007 | Eliasen et al. | |
| 2007/0100435 A1 | 5/2007 | Case et al. | |
| 2007/0118210 A1 | 5/2007 | Pinchuk | |
| 2007/0213813 A1 | 9/2007 | Von Segesser et al. | |
| 2007/0233228 A1 | 10/2007 | Eberhardt et al. | |
| 2007/0244545 A1 | 10/2007 | Birdsall et al. | |
| 2007/0244552 A1 | 10/2007 | Salahieh et al. | |
| 2007/0265701 A1 | 11/2007 | Gurskis et al. | |
| 2007/0288087 A1 | 12/2007 | Fearnot et al. | |
| 2008/0021552 A1 | 1/2008 | Gabbay | |
| 2008/0039934 A1 | 2/2008 | Styrc | |
| 2008/0071369 A1 | 3/2008 | Tuval et al. | |
| 2008/0082164 A1 | 4/2008 | Friedman | |
| 2008/0097595 A1 | 4/2008 | Gabbay | |
| 2008/0114452 A1 | 5/2008 | Gabbay | |
| 2008/0125853 A1 | 5/2008 | Bailey et al. | |
| 2008/0140189 A1 | 6/2008 | Nguyen et al. | |
| 2008/0147179 A1 | 6/2008 | Cai et al. | |
| 2008/0147183 A1 | 6/2008 | Styrc | |
| 2008/0154355 A1 | 6/2008 | Benichou et al. | |
| 2008/0154356 A1 | 6/2008 | Obermiller et al. | |
| 2008/0228264 A1 | 9/2008 | Li et al. | |
| 2008/0243245 A1 | 10/2008 | Thambar et al. | |
| 2008/0255662 A1 | 10/2008 | Stacchino et al. | |
| 2008/0262602 A1 | 10/2008 | Wilk et al. | |
| 2008/0269879 A1 | 10/2008 | Sathe et al. | |
| 2009/0112309 A1 | 4/2009 | Jaramillo et al. | |
| 2009/0138079 A1 | 5/2009 | Tuval et al. | |
| 2009/0157175 A1 | 6/2009 | Benichou | |
| 2010/0004740 A1 | 1/2010 | Seguin et al. | |
| 2010/0036484 A1 | 2/2010 | Hariton et al. | |
| 2010/0049306 A1 | 2/2010 | House et al. | |
| 2010/0082094 A1 | 4/2010 | Quadri et al. | |
| 2010/0087907 A1 | 4/2010 | Lattouf | |
| 2010/0131055 A1 | 5/2010 | Case et al. | |
| 2010/0168778 A1 | 7/2010 | Braido | |
| 2010/0168839 A1 * | 7/2010 | Braido | A61L 27/3604 623/1.26 |
| 2010/0185277 A1 * | 7/2010 | Braido | A61F 2/2433 623/2.18 |
| 2010/0191326 A1 | 7/2010 | Alkhatib | |
| 2010/0204781 A1 | 8/2010 | Alkhatib | |
| 2010/0204785 A1 | 8/2010 | Alkhatib | |
| 2010/0217382 A1 | 8/2010 | Chau et al. | |
| 2010/0249911 A1 | 9/2010 | Alkhatib | |
| 2010/0249923 A1 | 9/2010 | Alkhatib et al. | |

(56) References Cited

U.S. PATENT DOCUMENTS

| | | | |
|---|---|---|---|
| 2010/0286768 A1 | 11/2010 | Alkhatib | |
| 2010/0298931 A1 | 11/2010 | Quadri et al. | |
| 2011/0029072 A1 | 2/2011 | Gabbay | |
| 2011/0264206 A1 | 10/2011 | Tabor | |
| 2011/0295363 A1 | 12/2011 | Girard et al. | |
| 2012/0071969 A1* | 3/2012 | Li | A61F 2/2418 623/2.17 |
| 2012/0123529 A1 | 5/2012 | Levi et al. | |
| 2013/0018458 A1 | 1/2013 | Yohanan et al. | |
| 2013/0150956 A1 | 6/2013 | Yohanan et al. | |
| 2014/0277417 A1* | 9/2014 | Schraut | A61F 2/2403 623/2.17 |
| 2015/0073545 A1* | 3/2015 | Braido | A61F 2/2412 623/2.18 |
| 2015/0320556 A1 | 11/2015 | Levi et al. | |
| 2016/0317305 A1 | 11/2016 | Pelled et al. | |
| 2017/0014229 A1 | 1/2017 | Nguyen-Thien-Nhon et al. | |
| 2018/0147057 A1* | 5/2018 | Braido | A61F 2/2418 |

FOREIGN PATENT DOCUMENTS

| | | |
|---|---|---|
| DE | 202008009610 U1 | 12/2008 |
| EP | 0850607 A1 | 7/1998 |
| EP | 1000590 A1 | 5/2000 |
| EP | 1360942 A1 | 11/2003 |
| EP | 1584306 A1 | 10/2005 |
| EP | 1598031 A2 | 11/2005 |
| EP | 1926455 A2 | 6/2008 |
| FR | 2850008 A1 | 7/2004 |
| FR | 2847800 B1 | 10/2005 |
| WO | 9117720 A1 | 11/1991 |
| WO | 9716133 A1 | 5/1997 |
| WO | 9832412 A2 | 7/1998 |
| WO | 9913801 A1 | 3/1999 |
| WO | 0128459 A1 | 4/2001 |
| WO | 0149213 A2 | 7/2001 |
| WO | 0154625 A1 | 8/2001 |
| WO | 0156500 A2 | 8/2001 |
| WO | 0176510 A2 | 10/2001 |
| WO | 0236048 A1 | 5/2002 |
| WO | 0247575 A2 | 6/2002 |
| WO | 03047468 A1 | 6/2003 |
| WO | 06073626 A2 | 7/2006 |
| WO | 07071436 A2 | 6/2007 |
| WO | 08070797 A2 | 6/2008 |
| WO | 2009042196 A2 | 4/2009 |
| WO | 2010008548 A2 | 1/2010 |
| WO | 2010008549 A1 | 1/2010 |
| WO | 2010096176 A1 | 8/2010 |
| WO | 2010098857 A1 | 9/2010 |
| WO | 2014158710 A2 | 10/2014 |
| WO | 2015038458 A1 | 3/2015 |

OTHER PUBLICATIONS

Andersen, H.R., "Transluminal Catheter Implanted Prosthetic Heart Valves," International Journal of Angiology, Mar. 1998, pp. 102-106, vol. 7, No. 2.

Braido et al., U.S. Appl. No. 29/375,243, filed Sep. 20, 2010, titled "Surgical Stent Assembly".

Braido, Peter Nicholas, U.S. Appl. No. 291375,260, filed Sep. 20, 2010, titled "Forked Ends".

International Search Report and Written Opinion for Application No. PCT/US2015/025499 dated Jul. 15, 2015.

Knudsen, L.L. et al., "Catheter-implanted prosthetic heart valves," The International Journal of Artificial Organs, May 1993, pp. 253-262, vol. 16, No. 5.

Moazami, N. et al., Transluminal Aortic Valve Placement, ASAIO Journal, Sep.-Oct. 1996; pp. M381-M385, vol. 42, No. 5.

Quaden, R. et al., "Percutaneous aortic valve replacement: resection before implantation," European J. of Cardiothoracic Surgery, May 2005, pp. 836-840, vol. 27, No. 5.

Ruiz, C., "Overview of PRE-CE Mark Transcatheter Aortic Valve Technologies," Euro PCR, May 2010 (Powerpoint dated May 25, 2010).

Zegdi, R., MD, PhD et al., "Is It Reasonable to Treat All Calcified Stenotic Aortic Valves With a Valved Stent?" J. of the American College of Cardiology, Feb. 5, 2008, pp. 579-584, vol. 51, No. 5.

\* cited by examiner

LEAFLET ABRASION MITIGATION IN PROSTHETIC HEART VALVES

CROSS-REFERENCE TO RELATED APPLICATIONS

This application is a divisional of U.S. application Ser. No. 14/684,589, filed Apr. 13, 2015, which claims the benefit of the filing date of U.S. Provisional Patent Application No. 61/979,072 filed Apr. 14, 2014, the disclosure of which is hereby incorporated herein by reference.

BACKGROUND OF THE INVENTION

The present invention relates to heart valve replacement and, in particular, to collapsible prosthetic heart valves. More particularly, the present invention relates to collapsible prosthetic heart valves having leaflet abrasion mitigation features.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two common types of stents on which the valve structures are ordinarily mounted: a self-expanding stent and a balloon-expandable stent. To place such valves into a delivery apparatus and ultimately into a patient, the valve may first be collapsed or crimped to reduce its circumferential size and diameter.

When a collapsed prosthetic valve has reached the desired implant site in the patient (e.g., at or near the annulus of the patient's heart valve that is to be replaced by the prosthetic valve), the prosthetic valve can be deployed or released from the delivery apparatus and re-expanded to full operating use size. For balloon-expandable valves, this generally involves releasing the entire valve, assuring its proper location, and then expanding a balloon positioned within the valve stent. For self-expanding valves, on the other hand, the stent automatically expands as the sheath covering the valve is withdrawn.

BRIEF SUMMARY OF THE INVENTION

In some embodiments, a prosthetic heart valve includes a stent extending in a longitudinal direction, the stent being formed of a plurality of struts and having a plurality of commissure features, a collapsed condition and an expanded condition. A valve assembly may be secured to the stent, the valve assembly including a cuff and a plurality of leaflets, each of the leaflets having a free edge and being capable of alternating between an open position and a closed position. At least one buffer strip may be coupled to at least one of the plurality of struts and configured and arranged to minimize abrasion of the free edge of the leaflet in the open position.

In some embodiments, a prosthetic heart valve includes a stent extending in a longitudinal direction, the stent being formed of a plurality of struts forming cells and having a plurality of commissure features, a collapsed condition and an expanded condition. A valve assembly may be secured to the stent, the valve assembly including a fabric cuff and a plurality of leaflets, at least a portion of the cuff being disposed on an abluminal surface of the stent, each of the leaflets having a free edge and being arranged to open such that the free edge is adjacent the portion of the cuff disposed on the abluminal surface of the stent.

In some embodiments, a prosthetic heart valve, may include a stent extending in a longitudinal direction, the stent being formed of a plurality of struts forming cells and having a plurality of commissure features, a collapsed condition and an expanded condition. A valve assembly may be secured to the stent, the valve assembly including a cuff and a plurality of leaflets, the cuff being formed of a fabric and a second material different from the fabric, the cuff having commissure peaks and a plurality of midpeaks disposed between the commissure peaks, each of the leaflets having a free edge.

BRIEF DESCRIPTION OF THE DRAWINGS

Various embodiments of the present invention are described herein with reference to the drawings, wherein.

Various embodiments of the present invention will now be described with reference to the appended drawings. It will be appreciated that these drawings depict only some embodiments of the invention and are therefore not to be considered limiting of its scope.

DETAILED DESCRIPTION

As used herein, the term "proximal," when used in connection with a prosthetic heart valve, refers to the end of the heart valve closest to the heart when the heart valve is implanted in a patient, whereas the term "distal," when used in connection with a prosthetic heart valve, refers to the end of the heart valve farthest from the heart when the heart valve is implanted in a patient. Also, as used herein, the words "substantially," "generally" and "about" are intended to mean that slight variations from absolute are included within the scope of the structure or process recited.

Figure 1A:
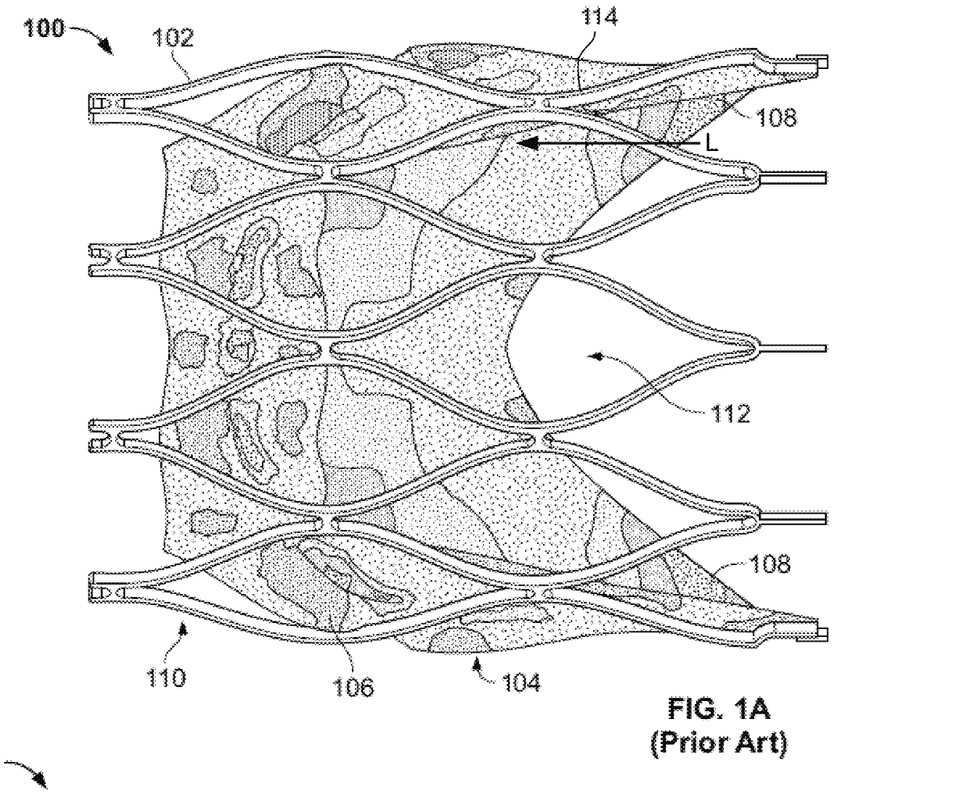
FIG. 1A is a partial side view of a prosthetic heart valve showing a potential strain distribution profile in the valve assembly.

FIG. 1A shows a typical collapsible prosthetic heart valve 100. The prosthetic heart valve 100 is designed to replace the function of the native aortic valve of a patient. Examples of collapsible prosthetic heart valves are described in International Patent Application Publication No. WO/2009/042196; U.S. Pat. Nos. 7,018,406; and 7,329,278, the disclosures of all of which are hereby incorporated herein by reference. Although the invention is described herein as applied to a prosthetic heart valve for replacing a native aortic valve, the invention is not so limited, and may be applied to prosthetic valves for replacing other types of cardiac valves.

The prosthetic heart valve 100 includes a stent or frame 102, which may be wholly or partly formed of any biocompatible material, such as metals, synthetic polymers, or biopolymers capable of functioning as a stent. Stent 102 is expandable and collapsible so that prosthetic heart valve 100 may be transitioned between a collapsed condition and an expanded condition. Suitable biopolymers include, but are not limited to, elastin, and mixtures or composites thereof. Suitable metals include, but are not limited to, cobalt, titanium, nickel, chromium, stainless steel, and alloys thereof, including nitinol. Suitable synthetic polymers for use as a stent include, but are not limited to, thermoplastics, such as polyolefins, polyesters, polyamides, polysulfones, acrylics, polyacrylonitriles, polyetheretherketone (PEEK), and polyaramides. The stent 102 may have an annulus section 110, an aortic section (not shown), and an intermediate section (not shown) disposed between the annulus and aortic sections. Each of the annulus section 110, the intermediate section, and the aortic section of the stent 102 includes a plurality of cells 112 connected to one another around the stent. The annulus section 110, the intermediate section, and the aortic section of the stent 102 may each include one or more annular rows of cells 112 connected to one another. For instance, the annulus section 110 may have two annular rows of cells 112. When the prosthetic heart valve 100 is in the expanded condition, each cell 112 may be substantially diamond shaped. Regardless of its shape, each cell 112 is formed by a plurality of struts 114. For example, a cell 112 may be formed by four struts 114.

The stent 102 may include commissure features or commissure posts (not shown) which may connect at least two cells 112 in the longitudinal direction of the stent 102. The commissure features may include eyelets that facilitate the suturing of a valve assembly and/or leaflets to the stent 102.

The prosthetic heart valve 100 also includes a valve assembly 104 attached within the annulus section 110 of the stent 102. U.S. Patent Application Publication No. 2008/0228264 and U.S. Patent Application Publication No. 2008/0147179, the entire disclosures of both of which are hereby incorporated herein by reference, describe suitable valve assemblies. The valve assembly 104 may be wholly or partly formed of any suitable biological material, fabric or a polymer. Examples of biological materials suitable for the valve assembly 104 include, but are not limited to, porcine or bovine pericardial tissue. Examples of polymers suitable for the valve assembly 104 include, but are not limited to, polyurethane and polyester.

The valve assembly 104 may include a cuff 106 disposed on the luminal surface of annulus section 110, on the abluminal surface of the annulus section, or on both surfaces, and the cuff may cover all or part of either or both of the luminal and abluminal surfaces of the annulus section. FIG. 1A shows cuff 106 disposed on the luminal surface of annulus section 110 so as to cover part of the annulus section while leaving another part thereof uncovered. In addition to the materials for forming valve assembly 104 noted above, the cuff 106 and/or any of the sutures described herein may include ultra-high-molecular-weight polyethylene. The valve assembly 104 may further include a plurality of leaflets 108 which collectively function as a one-way valve.

Figure 1B:
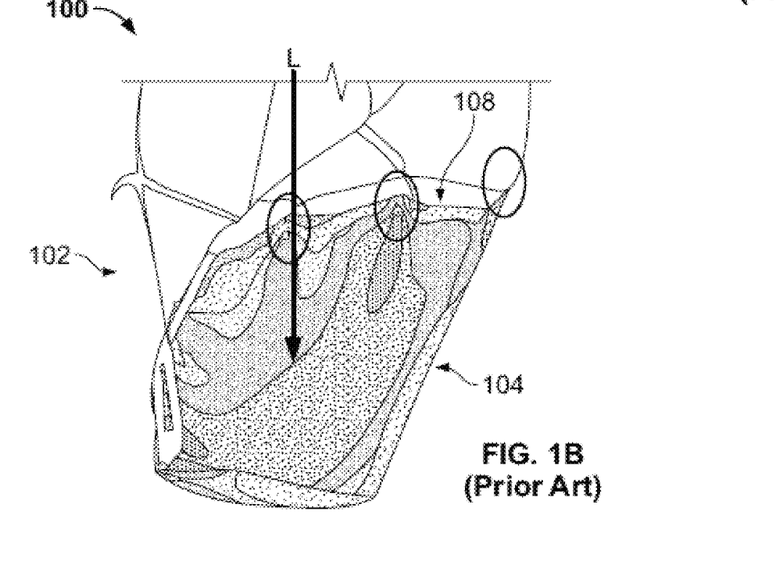
FIG. 1B is an enlarged partial view of the prosthetic heart valve of FIG. 1A showing the strain distribution in the leaflet.

The cuff 106 of the prosthetic heart valve 100 of FIG. 1A tends to experience relatively high strain and/or stress at certain locations. In such heart valves 100, the pressure of the blood that leaflets 108 keep from flowing back into the left ventricle may subject leaflets 108 to a load in the direction indicated by arrow L, shown in FIG. 1B. This load may cause high stress and/or strain on the cuff and/or leaflets, particularly where they are joined to one another. Moreover, a typical load may cause the cuff and/or leaflets to wear over time. To manage the increased stress and strain on the cuff 106, some conventional prosthetic heart valves have made the cuff thicker. However, thicker cuffs generally lead to a larger heart valve in the collapsed condition that is more difficult to deliver and implant. Instead of forming a thicker cuff, a different material such as fabric may be used.

Figure 2:
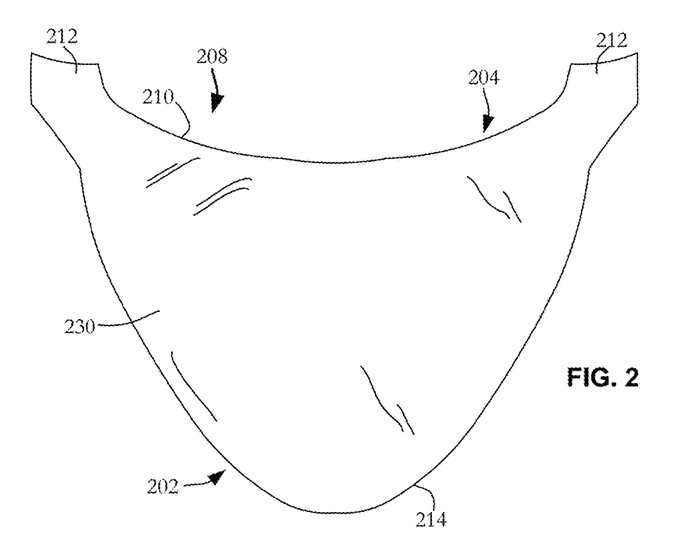
FIG. 2 is a side view of a leaflet showing regions prone to abrasion.

FIG. 2 illustrates one of several leaflets 208 that form a valve assembly. Leaflet 208 extends between proximal end 202 and distal end 204 and includes a belly 230 having a free edge 210 stretching between attachment regions 212, which couple the leaflet to the commissure features of a stent. A substantially parabolic belly contour 214 is formed between attachment regions 212 on the edge of leaflet 208 opposite free edge 210. In some examples, two leaflets 208 may be attached to each commissure feature of a stent. When the valve assembly is functioning properly, free edges 210 of leaflets 208 separate from one another to an open position to permit blood flow through the valve in one direction and coapt with one another in a closed position to impede blood flow in the opposite direction. In addition to the previously described strains, as leaflets 208 of the valve assembly open and close, certain regions of one leaflet will repeatedly contact a similar region on the other leaflets, and may repeatedly contact hardened calcium nodules or a feature of the heart valve due to valve distortion from the hardened calcium. When this occurs, abrasion may occur at said region of the leaflet or at a corresponding region of the cuff.

Figure 3:
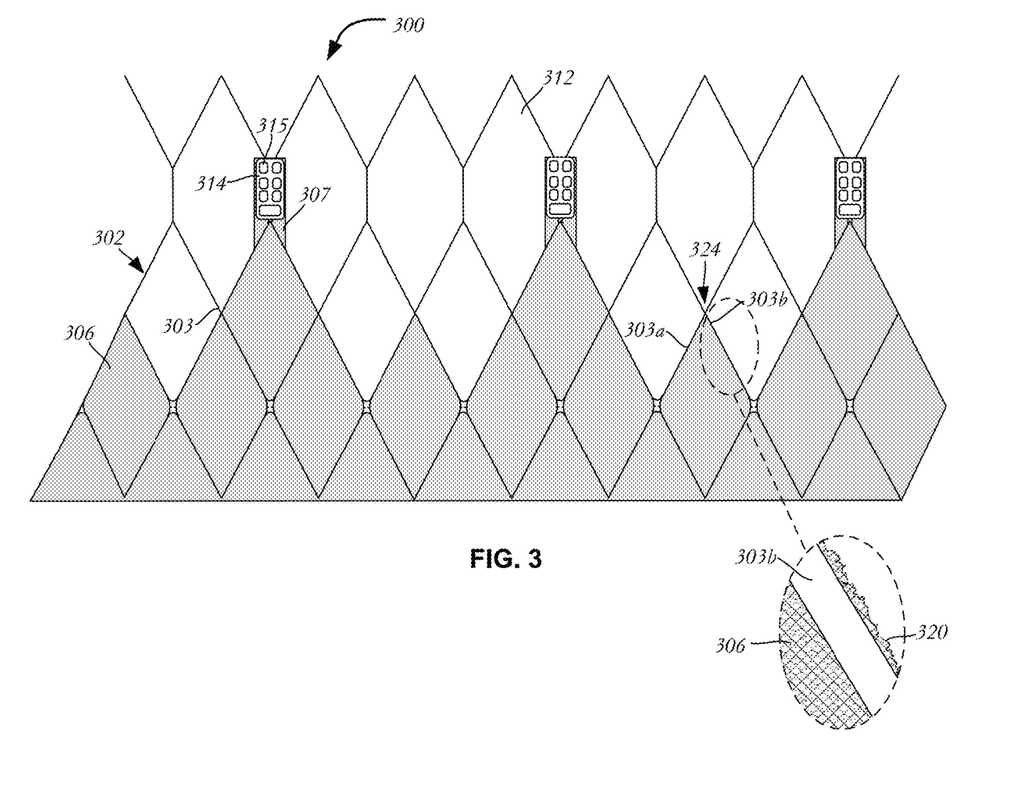
FIG. 3 is a highly schematic partial side view of a cuff disposed on the luminal surface of a stent.

FIG. 3 illustrates heart valve 300, which includes stent 302 formed of struts 303 and an attached cuff 306. For the sake of clarity, leaflets are not shown. Stent 302 may include one or more annular rows of cells 312 connected to one another and a plurality of spaced commissure features 314 to which attachment features of the leaflet may be secured via eyelets 315.

Cuff 306 is typically disposed on the luminal surface of annular stent 302 and includes three commissure peaks 307 for coupling with commissure features 314 of stent 302. As discussed above, cuff 306 may generally be formed of tissue, a polymer or a fabric. When formed of a fabric, cuff 306 may be cut from a large sheet into the shape shown in FIG. 3. The cut edges 320 of the cuff 306 may be jagged and abrasive, as shown in the detailed view of the cuff edge. As the leaflets repeatedly open and close, portions of leaflet 208 may contact the abrasive edges 320 of cuff 306, such as the edges 320 located adjacent struts 303a and 303b that define a midpeak 324 of cuff 306 located between commissure feature commissure peaks 307. To minimize abrasion and provide safe contact between the cuff and leaflets, several improvements to the cuff design are proposed, as described below.

Figure 4:
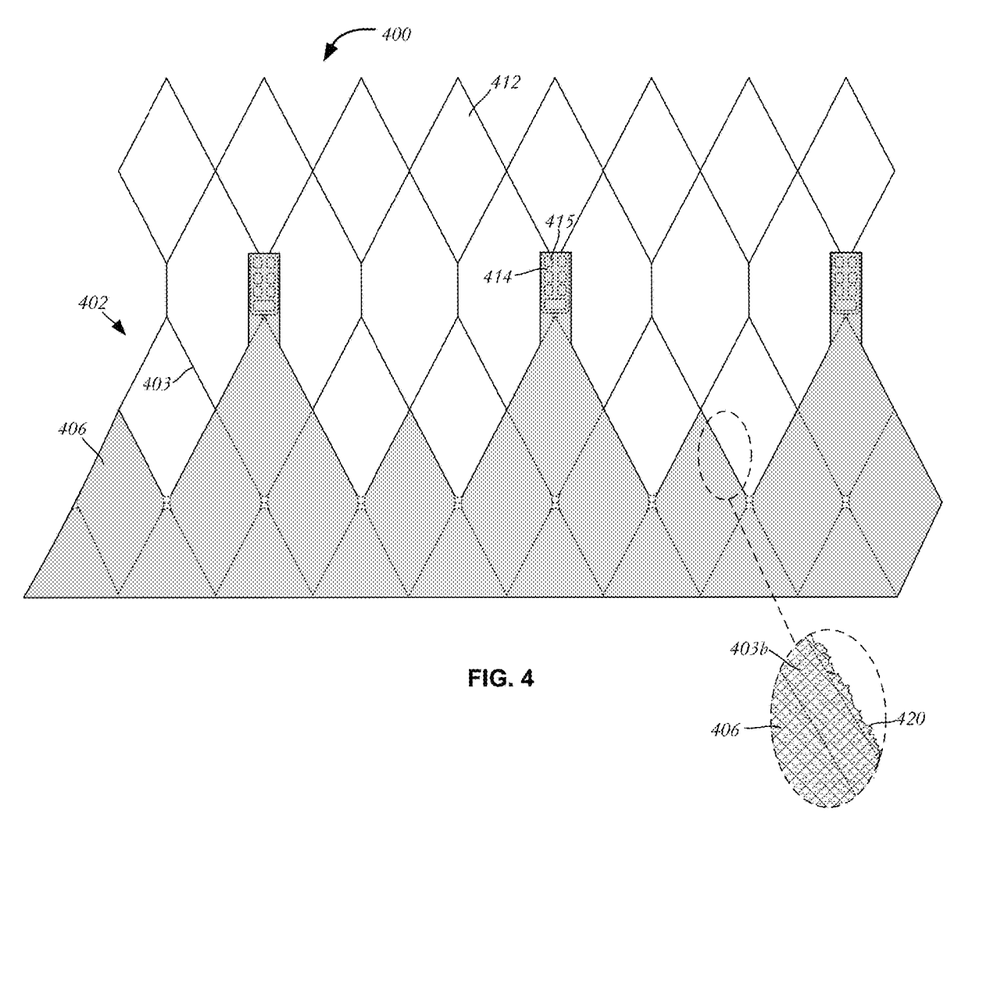
FIG. 4 is a highly schematic partial side view of a cuff entirely disposed on the abluminal surface of a stent.

FIG. 4 illustrates heart valve 400, which includes stent 402 formed of struts 403 are attached fabric cuff 406. For the sake of clarity, leaflets are not shown. Stent 402 may include one or more annular rows of cells 412 connected to one another and a plurality of spaced commissure features 414 to which attachment features of the leaflet may be secured via eyelets 415. In this first example, cuff 406 is disposed on the abluminal surface of stent 402 (e.g., as viewed from outside of the heart valve, cuff 406 overlies stent 402). By positioning fabric cuff 406 on the abluminal surface of the stent, struts (such as strut 403*b*) are positioned between the cuff 406 and the leaflets so that abrasion from the cut edges 420 of the cuff is minimized when the leaflets open. Additionally, cuff 406 may provide better sealing by being disposed on the abluminal surface.

Figure 5A:
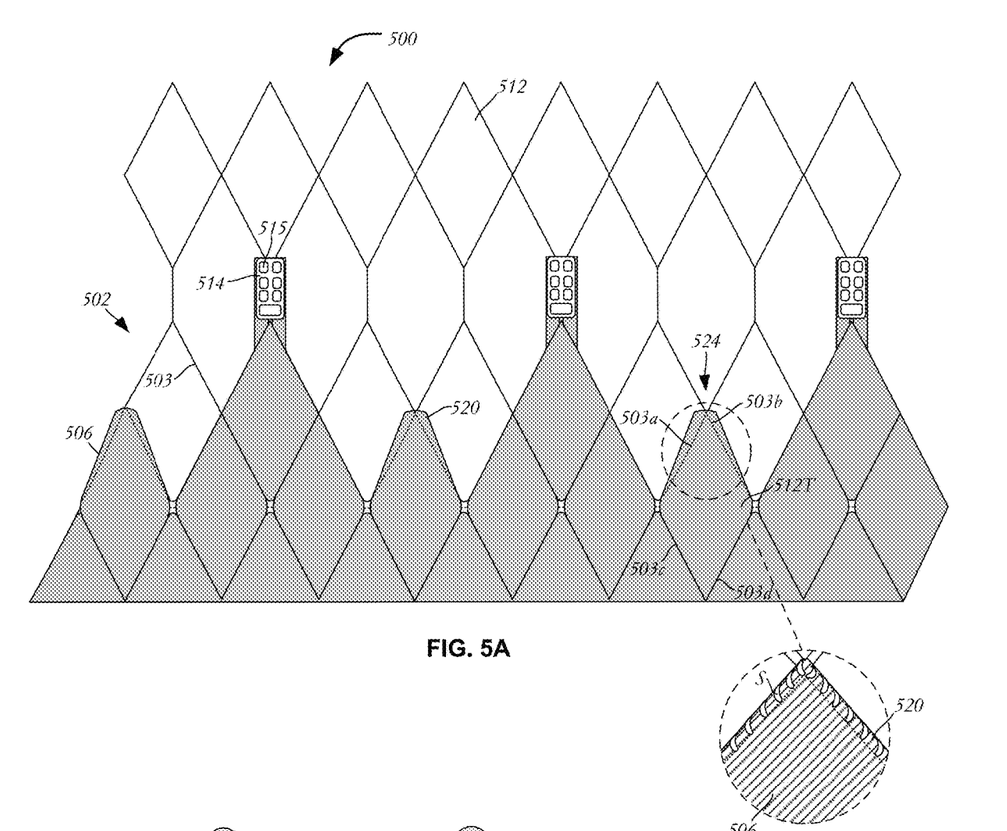
FIG. 5A is a highly schematic partial side view of a cuff having a cross-over region for passing from the luminal surface to the abluminal surface of a stent.
Figure 5B:
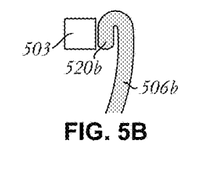
FIGS. 5B and 5C are highly schematic cross-sections showing two variations of the folding of cut edges.
Figure 5C:
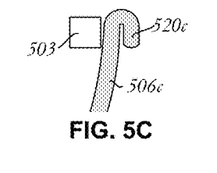

FIG. 5A is another example of a heart valve 500 configured to minimize abrasion of the leaflets. Heart valve 500 is similar to heart valve 300 and includes stent 502 formed of struts 503 and an attached fabric cuff 506. For the sake of clarity, leaflets are not shown. Stent 502 may include one or more annular rows of cells 512 connected to one another and a plurality of spaced commissure features 514 to which attachment features of the leaflet may be secured via eyelets 515. In this example, cuff 506 is almost entirely disposed on the luminal surface of stent 502 with certain exceptions. Triangular midpeaks 524 of cuff 506 are disposed on the abluminal surface of stent 502 by passing portions of the cuff from the luminal surface to the abluminal surface through cell 512T. Specifically, each midpeak 524 of cuff 506 is attached to struts 503*a* and 503*b* on the abluminal surface of stent 502, and is attached to struts 503*c* and 503*d* on the luminal surface of the stent. In this manner, cut edges 520 of fabric cuff 506 may be disposed away from the moving leaflets. Additionally, cut edges 520 disposed on the abluminal surface may be folded prior to attachment to struts 503. In a first variation (FIG. 5B), cut edge 520*b* of cuff 506*b* is folded toward strut 503 and hidden between cuff 506*b* and strut 503. In a second variation (FIG. 5C), cut edge 520*c* of cuff 506*c* may be folded away from strut 503. Regardless of whether cut edges 520 are folded and in which orientation, they may be secured to stent 502 with suture S as shown in the detailed view of FIG. 5A. With edges 520 hidden from the leaflets, the leaflets may open and close with little to no abrasion of the free edges.

Figure 6:
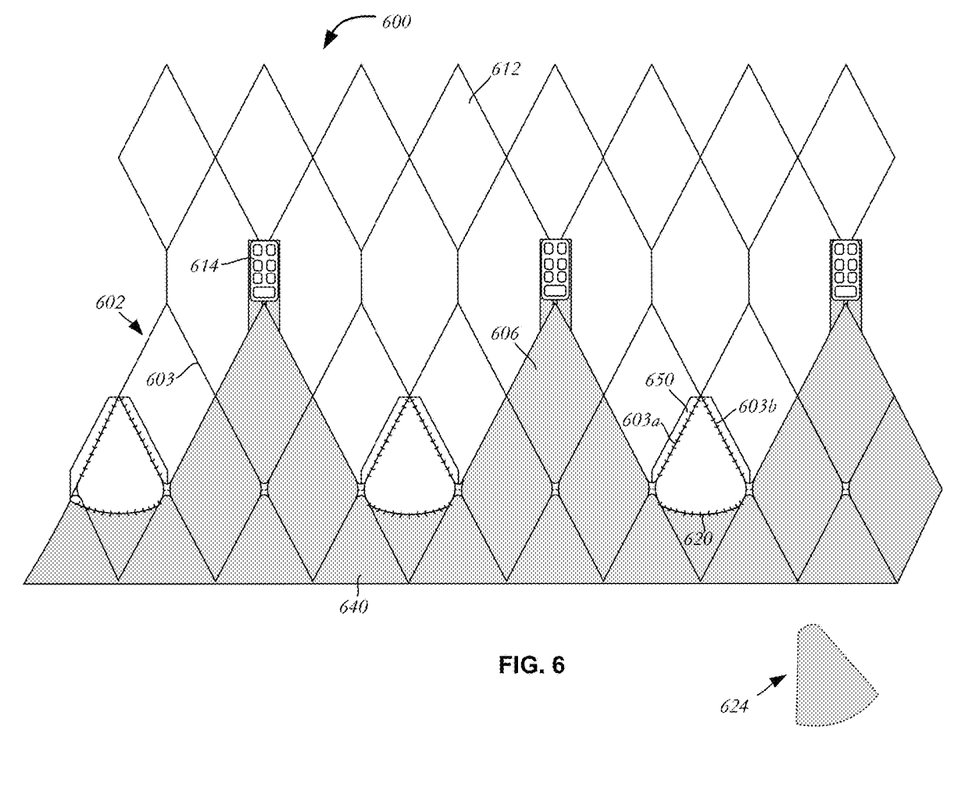
FIG. 6 is a highly schematic partial side view of a cuff disposed on the luminal surface of a stent, the cuff having buffers.

In another example, shown in FIG. 6, heart valve 600 includes stent 602 formed of struts 603 and an attached cuff 606. Stent 602 includes one or more annular rows of cells 612 connected to one another and a plurality of spaced commissure features 614 to which attachment features of the leaflet may be secured. In this example, cuff 606 is disposed on the luminal surface of stent 602. Unlike the previously described cuffs, cuff 606 includes two materials, a first material for forming main body 640 and a second material for forming the midpeaks. The second material forms discrete substantially triangular buffers 650 attached to main body 640.

The first material of main body 640 may be a fabric to reduce the crimp profile of the heart valve. In such cases, buffers 650 may be formed of a smooth second material, such as tissue or a polymer to minimize abrasion to the leaflets. As shown, midpeaks 624 may be removed from main body 640 along a cut edge 620, and each buffer 650 may be attached to cut edge 620 and to struts 603*a*, 603*b* using sutures as shown. In some examples, about 2 to 3 mm of buffers 650 may overlap with main body 640 and leaflets may be sutured through twin layers of buffers 650 and main body 640. As the leaflets (not shown) open and close, the free edges of the leaflets contact buffer 650, which provides a smoother contact region.

Figure 7:
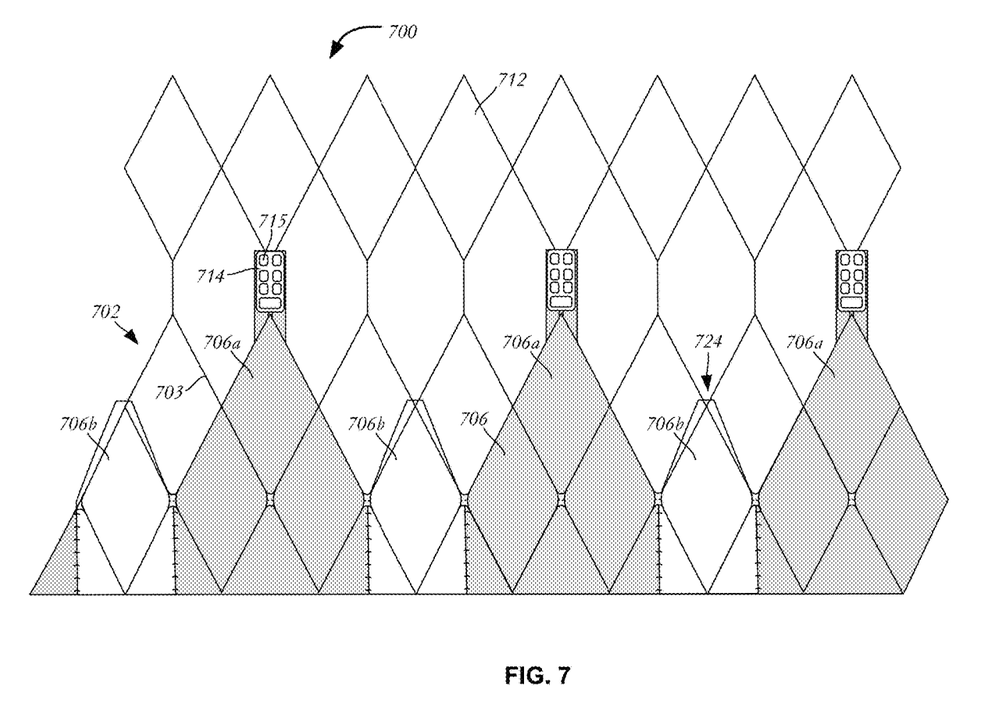
FIG. 7 is a highly schematic partial side view of a cuff disposed on the luminal surface of a stent, the cuff having alternating materials.

In FIG. 7, heart valve 700 includes stent 702 formed of struts 703 and an attached cuff 706. Stent 702 includes one or more annular rows of cells 712 connected to one another and a plurality of spaced commissure features 714 to which attachment features of the leaflet may be secured. In some cases, a fabric cuff is desired to reduce the crimp profile of the heart valve. Because of the abrasion potential of fabric, other materials may be used to reduce abrasion to the leaflets. For example, cuff 706 includes alternating fabric portions 706*a* and tissue portions 706*b*. Tissue portions 706*b* are disposed at midpeaks 724 between commissure features 714, while fabric portions 706*a* are disposed elsewhere including in the regions below commissure features 714. In this manner, the crimp profile is reduced through fabric portions 706*a* while abrasion is reduced via tissue portions 706*b*.

Figure 8:
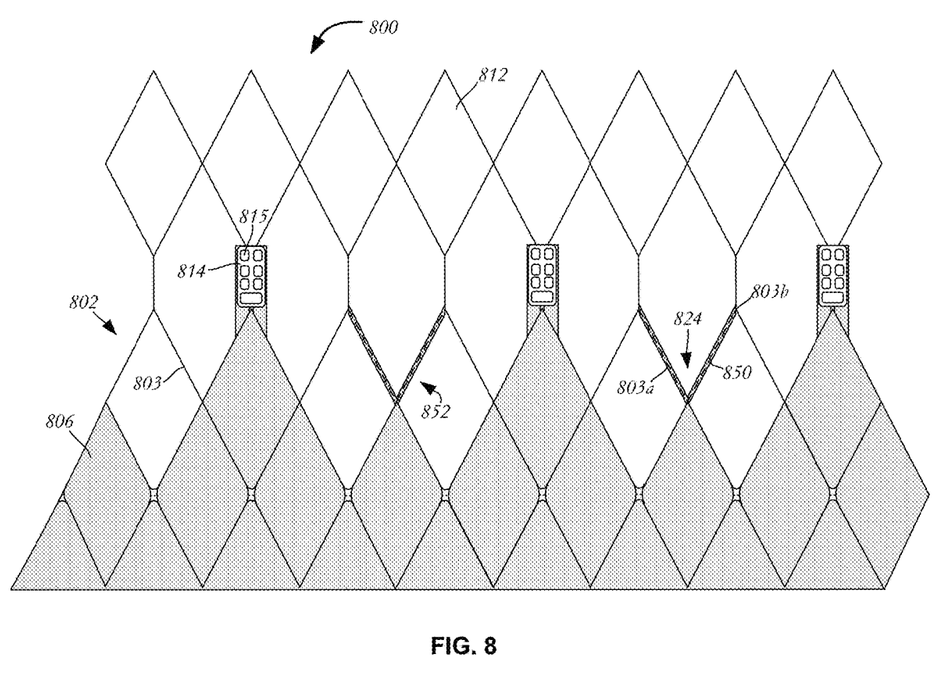
FIG. 8 is a highly schematic partial side view of a cuff disposed on the luminal surface of a stent, the cuff having buffer strips.

FIG. 8 illustrates heart valve 800 including stent 802 having struts 803, an attached cuff 806, rows of cells 812 and commissure features 814. It will be appreciated that heart valve 800 may often be implanted in a less than ideal native valve annulus. For example, the native valve annulus may be unevenly calcified or may have a cross-section that it not substantially circular (e.g., the valve annulus may be elliptical). Under such circumstances, the leaflets (not shown) may open and contact struts that are higher than cuff 806. In order to minimize abrasion of the leaflets by the struts, longitudinal buffer strips 850 may be secured to select ones of struts 803.

Buffer strips 850 may be formed of tissue, such as bovine or porcine pericardial tissue, or a polymer, such as ultra-high molecular weight polyethylene, polyurethane, polyester or suitable combinations thereof, and may be secured to the struts using sutures, glue, bioadhesive or other suitable techniques. Each buffer strip 850 extends along the length of a strut 803 and is wrapped around the strut. In FIG. 8, each buffer strip 850 is secured to certain struts, such as struts 803*a*, 803*b* located above a midpeak 824 of cuff 806. Strips 850 may be disposed in three groupings, each grouping forming a V-shaped cushion 852. It will be understood that, while FIG. 8 illustrates V-shaped cushions 852 located directly above midpeaks 824, the positioning of buffer strips is not so limited and buffer strips 850 may be coupled to other struts 803 and may form any number of suitable groupings. For example, a full row of cells 812 may include buffer strips 850 along the top struts of the cells, the bottom struts of the cells or all four struts of one or more cells.

Figure 9A:
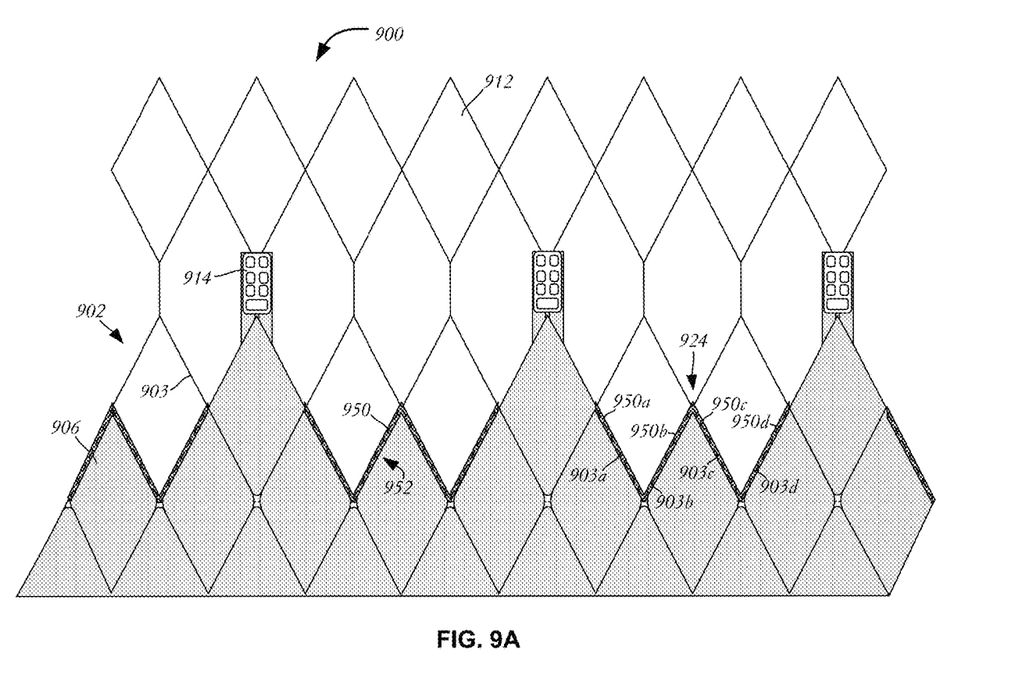
FIG. 9A is a highly schematic partial side view of another example of a cuff disposed on the luminal surface of a stent and having buffer strips.

FIG. 9A illustrates one such variation in which heart valve 900 includes stent 902 having struts 903, an attached cuff 906, rows of cells 912 and commissure features 914. In order to minimize abrasion of the leaflets by struts 903, buffer strips 950 may be secured to select struts. In this variation, buffer strips 950*a-d* are wrapped around struts 903*a-d* to form a W-shaped cushion 952, the center of each cushion 952 being formed adjacent a midpeak 924 of cuff 906. One W-shaped cushion 952 is disposed between each pair of commissure features 914, though it will be understood that the cushions alternatively may be formed of strips 950 disposed in various groupings and/or orientations, such as the V-shaped orientations described in connection with FIG. 8, or combinations of both the V-shaped and W-shaped cushions, or cushions formed in other shapes.

Figure 9B:
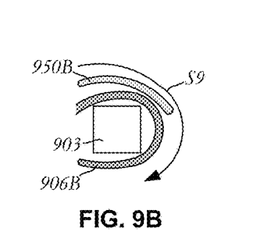
FIGS. 9B and 9C are highly schematic cross-sections showing two variations of the attachment of buffer strips to a strut.
Figure 9C:
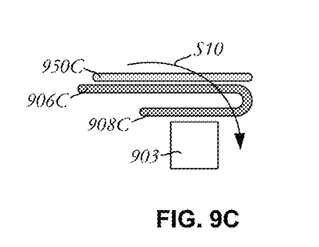

As previously discussed, strips 950 may be secured to selected struts using a variety of methods. FIGS. 9B and 9C illustrate two methods of attaching buffer strips 950 to strut 903. In FIG. 9B, cuff 906B is wrapped around strut 903. Buffer strip 950B is disposed over cuff 906B and wrapped over a portion of strut 903 so as to be positioned on the luminal surface of stent 902. A suture S9 is then wrapped with a whip-stitch around strip 950B, cuff 906B and strut 903 to secure all three together. In an alternative example, shown in FIG. 9C, cuff 906C is doubled over itself to create a second layer 908C. Both layers overlie strut 903 on the luminal side of stent 902. A flat buffer strip 950C is then disposed over cuff 906C and a suture S10 pierces through buffer strip 950C and the two layers of cuff 906C to secure buffer strip 950C and cuff 906C to strut 903 using a whip-stitch pattern.

In operation, any of the embodiments of the prosthetic heart valve described above may be used to replace a native heart valve, such as the aortic valve. The prosthetic heart valve may be delivered to the desired site in a patient (e.g., near a native aortic annulus) in a collapsed condition using any suitable delivery device. The delivery device may be introduced into the patient using a transfemoral, transapical, transseptal, transradial, transaortic, transsubclavian or other percutaneous approach. Once the delivery device has reached the target site, the user may deploy the prosthetic heart valve. Upon deployment, the prosthetic heart valve expands into secure engagement within the native valve annulus. When the prosthetic heart valve has been properly positioned inside the heart, it works as a one-way valve, allowing blood to flow in one direction and preventing blood from flowing in the opposite direction. Any of the variations shown above, such as, for example, the buffer strips, may be helpful in reducing contact between the leaflets and struts of the heart valve when opening and closing, thereby reducing the potential for of abrasion of the leaflets.

Although the invention herein has been described with reference to particular embodiments, it is to be understood that these embodiments are merely illustrative of the principles and applications of the present invention. For example, a prosthetic heart valve may include both buffer strips for reducing abrasion to the leaflets from the struts and an abluminal cuff to reduce abrasion to the leaflets from the cuff. Thus any combination of the preceding features may be used together and it is therefore to be understood that numerous modifications may be made to the illustrative embodiments and that other arrangements may be devised without departing from the spirit and scope of the present invention as defined by the appended claims.

In some embodiments, a prosthetic heart valve includes a stent extending in a longitudinal direction, the stent being formed of a plurality of struts and having a plurality of commissure features, a collapsed condition and an expanded condition. A valve assembly may be secured to the stent, the valve assembly including a cuff and a plurality of leaflets, each of the leaflets having a free edge and being capable of alternating between an open position and a closed position. At least one buffer strip may be coupled to at least one of the plurality of struts and configured and arranged to minimize abrasion of the free edge of the leaflet in the open position.

In some examples, the at least one buffer strip may be formed of tissue or a polymer, and/or may include three groupings of buffer strips, and/or may include multiple groupings of buffer strips, and/or the at least one buffer strip may include two buffer strips arranged in a V-shaped cushion, and/or the at least one buffer strip may include four buffer strips arranged in a W-shaped cushion, and/or the cuff may include a plurality of midpeaks disposed between an adjacent pair of the commissure features and the W-shaped cushions are centered about each of the plurality of midpeaks, and/or the heart valve may further include a suture configured to wrap around one of the plurality of struts and the at least one buffer strip, and/or the heart valve may further include a suture configured to pierce the cuff and the at least one buffer strip and to wrap around at least one of the plurality of struts.

In some embodiments, a prosthetic heart valve includes a stent extending in a longitudinal direction, the stent being formed of a plurality of struts forming cells and having a plurality of commissure features, a collapsed condition and an expanded condition. A valve assembly may be secured to the stent, the valve assembly including a fabric cuff and a plurality of leaflets, at least a portion of the cuff being disposed on an abluminal surface of the stent, each of the leaflets having a free edge and being arranged to open such that the free edge is adjacent the portion of the cuff disposed on the abluminal surface of the stent.

In some examples, the cuff may be entirely disposed on the abluminal surface of the stent, and/or the cuff may include midpeak portions and a remaining portion, the midpeak portions being disposed on the abluminal surface of the stent and the remaining portion being disposed on a luminal surface of the stent, and/or the midpeak portions may pass through select cells of the stent from the luminal surface of the stent to the abluminal surface of the stent, and/or the at least one edge of each of the midpeak portions may be folded.

In some embodiments, a prosthetic heart valve, may include a stent extending in a longitudinal direction, the stent being formed of a plurality of struts forming cells and having a plurality of commissure features, a collapsed condition and an expanded condition. A valve assembly may be secured to the stent, the valve assembly including a cuff and a plurality of leaflets, the cuff being formed of a fabric and a second material different from the fabric, the cuff having commissure peaks and a plurality of midpeaks disposed between the commissure peaks, each of the leaflets having a free edge.

In some examples, the fabric may alternate with the second material in the cuff, the second material forming the plurality of midpeaks of the cuff, and/or the second material may include tissue and/or a polymer, and/or the cuff may include triangular buffers formed from the second material, and/or each of the triangular buffers may include three edges, one of the edges being coupled to the fabric, and two of the edges being coupled to struts.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A prosthetic heart valve, comprising:
a stent extending in a longitudinal direction and having a collapsed condition and an expanded condition, the stent including a plurality of struts forming cells and a plurality of commissure features spaced apart in an annular direction of the stent, each of the commissure features having a width; and
a valve assembly secured to the stent, the valve assembly including a cuff and a plurality of leaflets, the cuff having commissure peaks and midpeaks disposed between adjacent commissure peaks, the cuff being formed of a fabric and a second material different from the fabric, the second material being located at discrete locations about a luminal surface of the stent and in the annular direction of the stent to minimize abrasion to the leaflets, each of the discrete locations being aligned with a respective one of the midpeaks in the longitudinal direction of the stent such that each of the discrete locations is annularly spaced apart from an adjacent one of the discrete locations by at least the width of the commissure features.

2. The prosthetic heart valve of claim 1, wherein the cuff includes alternating portions of the fabric and the second material.

3. The prosthetic heart valve according to claim 2, wherein the fabric portions and the second material portions alternate with one another in the annular direction of the stent.

4. The prosthetic heart valve of claim 1, wherein the second material includes tissue.

5. The prosthetic heart valve of claim 1, wherein the second material includes a polymer.

6. The prosthetic heart valve according to claim 1, wherein the second material forms a triangular buffer at each one of the midpeaks.

7. The prosthetic heart valve according to claim 6, wherein each one of the triangular buffers includes three edges, one of the edges being coupled to the fabric, and two of the edges being coupled to struts.

8. The prosthetic heart valve according to claim 1, wherein the second material is located at the midpeaks.

* * * * *